United States Patent
Yamashita et al.

(10) Patent No.: US 12,246,302 B2
(45) Date of Patent: Mar. 11, 2025

(54) BLOOD TREATMENT MATERIAL

(71) Applicant: Toray Industries, Inc., Tokyo (JP)

(72) Inventors: Kyohei Yamashita, Otsu (JP); Shungo Kanda, Otsu (JP); Hiroshi Takahashi, Otsu (JP)

(73) Assignee: Toray Industries, Inc., Tokyo (JP)

( * ) Notice: Subject to any disclaimer, the term of this patent is extended or adjusted under 35 U.S.C. 154(b) by 488 days.

(21) Appl. No.: 17/764,436

(22) PCT Filed: Oct. 2, 2020

(86) PCT No.: PCT/JP2020/037573
§ 371 (c)(1),
(2) Date: Mar. 28, 2022

(87) PCT Pub. No.: WO2021/066152
PCT Pub. Date: Apr. 8, 2021

(65) Prior Publication Data
US 2022/0362742 A1    Nov. 17, 2022

(30) Foreign Application Priority Data
Oct. 4, 2019   (JP) .................. 2019-183381

(51) Int. Cl.
  *B01J 20/26*   (2006.01)
  *B01D 15/08*   (2006.01)
  (Continued)

(52) U.S. Cl.
  CPC ............ *B01J 20/265* (2013.01); *B01D 15/08* (2013.01); *B01J 20/28011* (2013.01); *B01J 20/28023* (2013.01); *B01J 20/289* (2013.01); *B01J 20/321* (2013.01); *B01J 20/3219* (2013.01); *B01J 20/3257* (2013.01); *B01J 20/3295* (2013.01); *B01J 2220/52* (2013.01)

(58) Field of Classification Search
  CPC ............... B01J 20/265; B01J 20/28011; B01J 20/28023; B01J 20/289; B01J 20/321; B01J 20/3219; B01J 20/3257; B01J 20/3295; B01J 2220/52; B01D 15/08
  USPC ....... 502/7, 402; 424/501, 529, 534
  See application file for complete search history.

(56) References Cited

U.S. PATENT DOCUMENTS 5,051,185 A  *  9/1991  Watanabe .......... B01J 20/28033
                                                          502/402
2020/0215253 A1    7/2020  Ueno et al.

FOREIGN PATENT DOCUMENTS

EP    3 636 297 A1    4/2020
EP    3 679 966 A1    7/2020
(Continued)

OTHER PUBLICATIONS

Extended European Search Report dated Oct. 30, 2023, of counterpart European Patent Application No. 20873309.7.

*Primary Examiner* — Patricia L. Hailey
(74) *Attorney, Agent, or Firm* — DLA Piper LLP (US)

(57) ABSTRACT

A blood treatment material adsorbs and removes blood components such as activated leukocytes and inflammatory cytokines with a high efficiency. The blood treatment material includes a water-insoluble material in the form of fibers or particles, wherein the difference between the maximum value (RaA) and the minimum value (RaB) of the arithmetic average roughness (Ra) of the surface of the water-insoluble material, as calculated using a laser microscope, is from 0.30 to 1.50 μm.

7 Claims, 1 Drawing Sheet

(51) Int. Cl.
  *B01J 20/28* (2006.01)
  *B01J 20/289* (2006.01)
  *B01J 20/32* (2006.01)

(56) References Cited

FOREIGN PATENT DOCUMENTS

| | | | |
|---|---|---|---|
| JP | 4473324 B2 | 6/2010 | |
| JP | 6284818 B2 | 2/2018 | |
| WO | WO-2005026224 A1 * | 3/2005 | ........... A61L 2/0017 |
| WO | 2018/225764 A1 | 12/2018 | |
| WO | 2019/049961 A1 | 3/2019 | |
| WO | 2019/049962 A1 | 3/2019 | |

* cited by examiner

BLOOD TREATMENT MATERIAL

TECHNICAL FIELD

This disclosure relates to a blood treatment material.

BACKGROUND

In recent years, various types of blood treatment materials and columns packed with these materials have been developed for the purpose of selectively separating and adsorbing blood components such as activated leukocytes and inflammatory cytokines from blood.

As a means of improving the adsorption performance of blood treatment materials, a method in which a ligand that strongly interacts with a target substance such as a inflammatory cytokine or the like, is attached to the material surface, and a method in which the specific surface area of the portion of the material that comes into contact with blood is increased, are generally known.

For example, JP 4473324 B discloses that an adsorbent body made of a hydrophobic polymer resin such as a polyarylate resin, and is in the form of beads, hollow fibers or solid fibers whose surface has a center line average roughness of from 5 to 100 nm, is capable of further improving the adsorption performance of leukocytes and platelets.

JP 6284818 B discloses that a porous membrane laminate in which a porous membrane having a surface roughness (Sa) of 0.5 μm or less is laminated on at least one surface of a nonwoven fabric substrate, and which has a predetermined gas permeability and tensile strength, can be used as a filter for medical use.

WO 2018/225764 discloses that a water-insoluble carrier to the surface of which a compound containing a functional group having an electric charge is bound can be suitably used for the removal of activated leukocyte-activated platelet complexes, by restricting the center line average roughness of the above-described surface within a specific range.

WO 2019/049962 discloses that a material which contains a water-insoluble carrier to the surface of which a nitrogen-containing compound is bound can be suitably used for the adsorption of immunosuppressive leukocytes, particularly, LAP-positive lymphocytes or LAP-positive monocytes, by restricting the arithmetic average roughness of the above-described surface within a predetermined range.

In JP '324, WO '764 or WO '962, a technique focused on the center line average roughness or the arithmetic average roughness is disclosed. The term "center line average roughness" as used therein is an index that quantifies the surface roughness as defined in JIS B 0601: 1994. The "arithmetic average roughness" is a term which has been used after JIS B 0601: 2001, and has the same meaning as the center line average roughness.

Each of JP '324, WO '764 and WO '962 discloses the relationship between the surface roughness and the adsorption performance. JP '324 specifically discloses the center line average roughness of the surface of the beads which are substantially perfect spheres, in Examples 1 to 3, and describes that it is possible to simultaneously adsorb leukocytes and platelets, by adjusting the center line average roughness within the range of from 5 to 100 nm. However, when an excessive amount of platelets adhere to the adsorbent body, the material surface is covered with platelets, and there is a risk that the adsorption of leukocytes and cytokines, which are adsorption targets, may be inhibited. Further, JP '324 is silent about the relationship between the direction of the center line average roughness and the adsorption performance. WO '764 describes the relationship between the developed length ratio or the center line average roughness of the material surface and activated leukocyte-activated platelet complexes, but is silent about the relationship between the direction of the center line average roughness and the adsorption performance. WO '962 describes that the value in the longitudinal direction is measured as the arithmetic average roughness, in a material having an orientation such as fibers. However, WO '962 is silent about the arithmetic average roughness in other directions and the relationship with the adsorption performance.

On the other hand, JP '818 describes the relationship between the surface roughness and how easily air bubbles adhere during the filtration or the filtration efficiency, but is silent about the relationship between the surface roughness and the adsorption performance. Further, JP '818 describes only the surface roughness (Sa) per unit area of the nonwoven fabric including a plurality of single fibers, and is silent about the surface roughness per single fiber.

In performing extracorporeal circulation using a column packed with a carrier such as one described above, a smaller amount of blood taken from a patient leads to a lesser burden on the patient. Therefore, a carrier having a further improved adsorption efficiency is demanded.

Accordingly, it could be helpful to provide a blood treatment material that adsorbs and removes blood components such as activated leukocytes and inflammatory cytokines, with a high efficiency.

SUMMARY

We found that blood components such as activated leukocytes and inflammatory cytokines can be adsorbed with a high efficiency, by introducing anisotropy to the arithmetic average roughness of the material surface.

We thus provide [1] to [8]:

[1] A blood treatment material comprising a water-insoluble material in the form of fibers or particles,
  wherein the difference between the maximum value (RaA) and the minimum value (RaB) of the arithmetic average roughness (Ra) of the surface of the water-insoluble material, as calculated using a laser microscope, is 0.30 to 1.50 μm.

[2] The blood treatment material according to [1], wherein the difference is 0.33 to 1.00 μm.

[3] The blood treatment material according to [1] or [2], wherein the maximum value (RaA) is 0.50 μm or more.

[4] The blood treatment material according to any one of [1] to [3],
  wherein a ligand containing an amino group is bound to the surface of the water-insoluble material; and
  wherein the content of the amino group is 0.20 to 3.00 mmol per 1 g in dry weight of the water-insoluble material.

[5] The blood treatment material according to any one of [1] to [4],
  wherein the water-insoluble material is in the form of fibers; and
  wherein the direction of measurement of the laser microscope in which the arithmetic average roughness (Ra) of the surface of the water-insoluble material is minimum, is the fiber longitudinal direction.

[6] The blood treatment material according to any one of [1] to [5],
  wherein the water-insoluble material is in the form of sea-island composite fibers;

wherein the sea component of the sea-island composite fibers is selected from the group consisting of polystyrene, a derivative of polystyrene, polysulfone and a derivative of polysulfone, and a mixture thereof; and wherein the island component of the sea-island composite fibers is selected from the group consisting of polypropylene, polyethylene and a polypropylene/polyethylene copolymer, and a mixture thereof.

[7] The blood treatment material according to any one of [1] to [6], wherein the blood treatment material is used for the adsorption and removal of activated leukocytes and/or inflammatory cytokines.

[8] A blood purification column comprising the blood treatment material according to any one of [1] to [7].

Our blood treatment material is capable of adsorbing activated leukocytes and inflammatory cytokines with a high efficiency, and can be used as an adsorption carrier for use in extracorporeal circulation.

Figure 1:
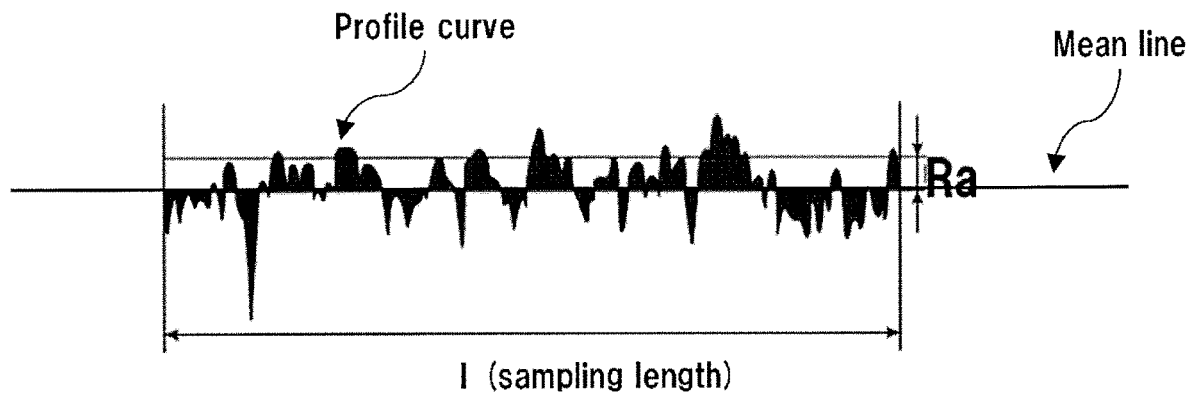
FIG. 1 is a diagram illustrating the method of determining the arithmetic average roughness.

REFERENCE SIGNS LIST 1. single fiber
2. single fiber diameter (fiber diameter)

DETAILED DESCRIPTION

Our materials will now be described in detail.

Our blood treatment material is characterized in that the material contains a water-insoluble material in the form of fibers or particles, and that the difference between the maximum value (RaA) and the minimum value (RaB) of the arithmetic average roughness (Ra) of the surface of the water-insoluble material, as calculated using a laser microscope, is 0.30 to 1.50 μm.

The term "blood treatment" refers to treating a patient with a blood-derived disease, by adsorbing and removing a blood component(s) using a suitable material.

The term "blood component" refers to a component contained in blood such as, for example, a cell in blood, or a humoral factor in blood.

The term "cell in blood" refers to a cell contained in blood. Examples thereof include: leukocyte components such as granulocytes, monocytes, neutrophils and eosinophils; erythrocytes; platelets; activated platelets; and activated leukocyte-activated platelet complexes. When the blood treatment material is used for the purpose of treating inflammatory diseases, activated leukocytes are preferred as the substances to be adsorbed.

The term "humoral factor in blood" refers to an organic substance dissolved in blood. Specific examples thereof include: urea; proteins such as β2-microglobulin, cytokines, IgE and IgG; and polysaccharides such as lipopolysaccharides (LPS). Among these, urea, proteins such as cytokines, and polysaccharides such as LPS are preferred as the substances to be adsorbed. Further, when the blood treatment material is used for the purpose of treating inflammatory diseases, inflammatory cytokines are more preferred as the substances to be adsorbed.

The term "inflammatory cytokines" refer to a group of proteins produced from various types of cells including immunocompetent cells, due to stimuli such as infections and traumas, and released extracellularly to act. Examples thereof include interferon-α, interferon-β, interferon-γ, interleukin-1 to interleukin-15, tumor necrosis factor-α, tumor necrosis factor-β, high-mobility group box-1, erythropoietin and monocyte chemotactic factors.

The term "blood treatment material" refers to a material containing a water-insoluble material in at least a part of the material, and the definition thereof include one consisting solely of a water-insoluble material, and one in which a water-insoluble material is fixed to, or mixed with, a suitable reinforcing material. The operation of fixing or mixing can be carried out before shaping the material, or after shaping the material.

The term "water-insoluble material" refers to a material insoluble in water. The expression "insoluble in water" means that the change in dry weight before and after introducing the water-insoluble material into water is 1% or less. The change in dry weight described above is the proportion of the dry weight of the solid content that remained after immersing the water-insoluble material in water, with respect to the dry weight of the material before the immersion. Specifically, the solid content described above is that remained after immersing the water-insoluble material in 37° C. water in an amount 9 times the dry weight thereof, for one hour, then picking it up with forceps or the like, and vacuum drying the remaining water at a temperature of 50° C. or lower. When the material is not insolubilized, there is a risk that dissolved substances of the material may increase when the material is actually used, and thus is not preferred in terms of safety.

The term "dry weight" refers to the weight of a solid in a dry state. The expression "solid in a dry state" refers to a solid in a state where the amount of liquid component contained in the solid is 1% by weight or less. When a solid is heated and dried at 80° C. for 24 hours at the atmospheric pressure after measuring the weight of the solid, and if the amount of decrease in weight of the remaining solid is 1% by weight or less of the weight of the solid before the drying, the solid is regarded to be in a dry state.

The term "to be adsorbed/adsorption" refers to a state in which a substance adheres to a material and cannot be easily released therefrom, or means that the substance and the material are in the adsorption equilibrium state. While the principle of the adsorption is not particularly limited, the adsorption refers to a state in which a substance is adhered by an intermolecular force such as electrostatic interaction, hydrophobic interaction, hydrogen bonding or van der Waals force, or a state in which a substance is physically adhered, for example, in cell adhesion or leukocyte phagocytosis.

Examples of a component constituting the water-insoluble material include polymers selected from the group consisting of: polyethylene terephthalate, polybutylene terephthalate, polyaromatic vinyl compounds, polyesters, polysulfone, polyethersulfone, polystyrene, and derivatives thereof such as polycarbonate, polyether ketone, polyether ether ketone, polyphenylene sulfide, polyphenol, polyphenylene ether, polyphenylene ethynylene, polyamideimide, polystyrene sulfonic acid, poly(4-methylstyrene), poly(4-ethylstyrene), poly(4-isopropylstyrene), poly(2-chlorostyrene), poly(4-chlorostyrene), poly(3-hydroxystyrene), poly(4-methoxystyrene), poly(4-carboxystyrene), poly(4-nitrostyrene), poly(4-chloromethylstyrene), poly(2,4-dimethylstyrene), poly(2,5-dichlorostyrene), poly(2,4,5-tribromo styrene), poly(2,3,4,5,6-pentafluorostyrene, sulfonated polysulfone and sulfonated polyethersulfone), but not particularly limited thereto, polyvinyl alcohol, cellulose acetate and polyacrylonitrile, as well as homopolymers, copolymers and mixtures thereof. When allowing a ligand to bind to the surface, the component constituting the water-insoluble material is preferably a polymer selected from the group consisting of polystyrene, a derivative of polystyrene, polysulfone, a derivative of polysulfone, polyethersulfone and a derivative of polyethersulfone, and a mixture thereof, more preferably a polymer selected from the group consisting of polystyrene, a derivative of polystyrene, polysulfone and a derivative of polysulfone, and a mixture thereof, and still more preferably polystyrene, because such a polymer contains a large number of aromatic rings per unit weight, and facilitates the immobilization of amino groups. Examples of the derivative of polystyrene include polystyrene sulfonic acid, poly(4-methylstyrene), poly(4-ethylstyrene), poly(4-isopropylstyrene), poly(2-chlorostyrene), poly(4-chlorostyrene), poly(3-hydroxystyrene), poly(4-methoxystyrene), poly(4-carboxystyrene), poly(4-nitrostyrene), poly(4-chloromethylstyrene), poly(2,4-dimethylstyrene) and poly(2,5-dichlorostyrene). Examples of the derivative of polysulfone include sulfonated polysulfone. Examples of the derivative of polyethersulfone include sulfonated polyethersulfone.

The water-insoluble material is suitably in the form of fibers or particles, because of their large specific surface area and excellent handleability.

When the water-insoluble material is in the form of fibers, the water-insoluble material is preferably in the form of a yarn bundle, a yarn, a net, a knitted fabric, a woven fabric, a felt, a net or the like, obtained by processing the fibers. The water-insoluble material is more preferably in the form of a yarn bundle, a knitted fabric, a woven fabric, a felt or a net, in view of their large specific surface area and low flow path resistance. Of these, a knitted fabric, a felt or a net can be produced by a known method, using the fibers as a raw material. Examples of the method of producing a felt include methods such as wet process, carding, air-laying, spun-bonding and melt blowing. Examples of the method of producing a knitted fabric or a net include methods such as plain weaving and circular knitting. In particular, a knitted fabric produced by circular knitting is preferred from the viewpoint of a high packing weight per unit volume, and of being packed into a blood purification device.

When the water-insoluble material is in the form of fibers, the water-insoluble material is preferably in the form of sea-island composite fibers, from the viewpoint of maintaining the strength per single fiber. Fibers fixed to, or mixed with a suitable reinforcing material may be included in the definition of the sea-island composite fibers. For example, the island component to be described later can be regarded as a reinforcing material. When an island component which is insoluble in water is used, in particular, the island component is regarded as a part of the water-insoluble material.

The sea component of the sea-island composite fibers is preferably a material insoluble in water, and having a structure capable of allowing a ligand to bind to the surface. Examples of the sea component include polymers selected from the group consisting of: polyethylene terephthalate, polybutylene terephthalate, polyaromatic vinyl compounds, polyesters, polysulfone, polyethersulfone, polystyrene, and derivatives thereof such as polycarbonate, polyether ketone, polyether ether ketone, polyphenylene sulfide, polyphenol, polyphenylene ether, polyphenylene ethynylene, polyamideimide, polystyrene sulfonic acid, poly(4-methylstyrene), poly(4-ethylstyrene), poly(4-isopropylstyrene), poly(2-chlorostyrene), poly(4-chlorostyrene), poly(3-hydroxystyrene), poly(4-methoxystyrene), poly(4-carboxystyrene), poly(4-nitrostyrene), poly(4-chloromethylstyrene), poly(2,4-dimethylstyrene), poly(2,5-dichlorostyrene), poly(2,4,5-tribromo styrene), poly(2,3,4,5,6-pentafluorostyrene, sulfonated polysulfone and sulfonated polyethersulfone, and polyvinyl alcohol, and mixtures thereof. When allowing a ligand to bind to the surface, the sea component is preferably a polymer selected from the group consisting of polystyrene, a derivative of polystyrene, polysulfone, a derivative of polysulfone, polyethersulfone and a derivative of polyethersulfone, and a mixture thereof, more preferably a polymer selected from the group consisting of polystyrene, a derivative of polystyrene, polysulfone and a derivative of polysulfone, and a mixture thereof, and still more preferably polystyrene, because such a polymer contains a large number of aromatic rings per unit weight, and facilitates the immobilization of amino groups. The derivative as used herein refers to a compound having from 1 to 2 substituents in the aromatic ring. Examples of the derivative of polystyrene include polystyrene sulfonic acid, poly(4-methylstyrene), poly(4-ethylstyrene), poly(4-isopropylstyrene), poly(2-chlorostyrene), poly(4-chlorostyrene), poly(3-hydroxystyrene), poly(4-methoxystyrene), poly(4-carboxystyrene), poly(4-nitrostyrene), poly(4-chloromethylstyrene), poly(2,4-dimethylstyrene) and poly(2,5-dichlorostyrene). Examples of the derivative of polysulfone include sulfonated polysulfone. Examples of the derivative of polyethersulfone include sulfonated polyethersulfone.

The island component of the sea-island composite fibers may be, for example, a polymer selected from the group consisting of polypropylene, polyethylene and a polypropylene/polyethylene copolymer, and a mixture thereof, because, at the time of introducing a ligand to the surface (sea component) of the fiber, such a polymer is capable of following the changes in mechanical properties such as swelling and shrinking of the sea component, and plays a role of a core or a reinforcing material in which the changes in chemical and mechanical properties caused by chemicals are small. Because of its capability to form a good cross section in a composite spun yarn, the island component is more preferably a polymer selected from the group consisting of polypropylene, a polypropylene/polyethylene copolymer and a mixture thereof, and still more preferably polypropylene.

The combination of the sea component and the island component of the sea-island composite fibers is preferably, for example, a combination in which the sea component is a polymer selected from the group consisting of polystyrene, a derivative of polystyrene, polysulfone, a derivative of polysulfone, polyethersulfone and a derivative of polyethersulfone, and a mixture thereof, and the island component is a polymer selected from the group consisting of polypropylene, polyethylene and a polypropylene/polyethylene copolymer, and a mixture thereof; more preferably a combination in which the sea component is a polymer selected from the group consisting of polystyrene, a derivative of polystyrene, polysulfone and a derivative of polysulfone, and a mixture thereof, and the island component is a polymer selected from the group consisting of polypropylene, polyethylene and a polypropylene/polyethylene copolymer, and a mixture thereof; still more preferably a combination in which the sea component is a polymer selected from the group consisting of polystyrene, a derivative of polystyrene, polysulfone and a derivative of polysulfone, and a mixture thereof, and the island component is a polymer selected from the group consisting of polypropylene, a polypropylene/polyethylene copolymer and a mixture thereof; and yet still more preferably a combination in which the sea component is polystyrene, and the island component is polypropylene.

The fibers such as sea-island composite fibers constituting the water-insoluble material may have a single fiber diameter (referred to as "fiber diameter") of any size. However, the single fiber diameter is preferably 3 to 200 µm, more preferably 5 to 50 µm, and still more preferably 10 to 40 µm, from the viewpoints of improving the contact area with a substance to be adsorbed, and maintaining the strength of the material. Any preferred lower limit value can be combined with any preferred upper limit.

The term "single fiber diameter" refers to the mean value of the measured values of the fiber diameter obtained by: collecting 10 small sample pieces of fiber at random; taking a photograph of each sample at a magnification of 1,000 to 3,000 times, using a scanning electron microscope; measuring the fiber diameter at 10 points per each photograph (100 points in total); and calculating the mean value of the measured values.

The single fiber diameter of the sea-island composite fibers constituting the water-insoluble material can be decreased, by decreasing the amount of polymer discharged during spinning, and increasing the winding speed to a high level. Further, when introducing a ligand, the single fiber diameter of the sea-island composite fibers can be increased, by swelling the fibers by solvent impregnation at the time of introducing the ligand. Accordingly, the single fiber diameter of the sea-island composite fibers can be controlled within a target range, by appropriately adjusting the conditions.

When the water-insoluble material is in the form of particles, the particles preferably have a diameter of 1 to 500 µm, from the viewpoint of ensuring a sufficient specific surface area for adsorbing a target substance.

The term "arithmetic average roughness (Ra)" is an index that quantifies the surface flatness as defined in JIS B 0601: 2001, and refers to the irregularity of the blood contact surface of the water-insoluble material. Specifically, the arithmetic average roughness (Ra) can be determined, using a laser microscope (for example, an ultra-deep 3D-shape measuring microscope, VK-9710, manufactured by Keyence Corporation) which has a laser confocal optical system, which is capable of two-dimensional scanning, and which is equipped with a line roughness analysis function (for example, a shape analysis application, VK-H1A1/VK-H2A1, manufactured by Keyence Corporation), as follows. Namely, an image of the surface of the material which has been dried in advance is captured at an objective lens magnification of 50 times, a line segment is extracted from the resulting image, and the arithmetic average roughness (Ra) is calculated from the extracted sampling length l. FIG. 1 shows the sampling length l (µm), the profile and the mean line, of the extracted portion, and the arithmetic average roughness is the value obtained by totaling and averaging the absolute values (µm) of the deviation from the mean line to the profile in this extracted portion. The method of calculating the arithmetic average roughness is as shown in Equation (1). In Equation (1), Ra stands for the arithmetic average roughness, and f(x) is a function representing the surface irregularity at an arbitrary position x in the laser microscope image.

$$Ra = \frac{1}{\ell} \int_0^\ell |f(x)| dx \quad (1)$$

The material to be measured needs to be dried in advance, taking into consideration the change in shape due to surface hydration, and the change in the state of wetness caused by the evaporation of moisture.

The term "mean line" refers to the line obtained by replacing the profile with a straight line by the least-squares method, as defined in JIS B 0601: 2001.

The term "profile" refers to the curve obtained by tracing the outline of the material surface, when an image of the surface of the material to be measured is captured using a laser microscope, as shown in FIG. 1. The profile is also referred to as "measured sectional curve."

The "maximum value of the arithmetic average roughness (Ra)" refers to the arithmetic average roughness (Ra) having the maximum value, of the values of the arithmetic average roughness (Ra) of the surface of the water-insoluble material that have each been determined by the method described above. Specifically, in accordance with the method of calculating the "arithmetic average roughness (Ra)" described above, line segments at 10 locations are extracted at random from the resulting image such that the respective line segments are not in parallel with each other. This operation is performed for each of the images captured in three different visual fields, the arithmetic average roughness (Ra) is calculated for each of the line segments of the total of 30 locations that have been extracted from the images in the three visual fields, and the arithmetic average roughness (Ra) having the maximum value, of all the calculated values, is defined as RaA. The "minimum value of the arithmetic average roughness (Ra)" can also be determined in the same manner as the method described above. Specifically, the arithmetic average roughness (Ra) having the minimum value, of the values of the arithmetic average roughness (Ra) calculated from the extracted line segments of the total of 30 locations, is defined as RaB. When the water-insoluble material is in the form of fibers, the line segments in at least the fiber longitudinal direction and the fiber transverse direction are extracted.

The maximum value (RaA) of the arithmetic average roughness (Ra) of the surface of the water-insoluble material is preferably adjusted to 0.50 µm or more, more preferably 0.60 µm or more, and still more preferably 0.63 µm or more. This is because, when sufficient irregularities are formed on the surface of the water-insoluble material, the cells in blood can easily recognize the material, and when the material has a sufficient specific surface area, humoral factors in blood can be adsorbed and removed with a high efficiency. Further, the maximum value (RaA) of the arithmetic average roughness (Ra) of the surface is preferably 3.0 µm or less, in view of the risk of the generation of fine particles. For example, the maximum value (RaA) of the arithmetic average roughness (Ra) of the surface of the water-insoluble material is 0.50 µm or more and 3.0 µm or less, 0.50 µm or more and 2.0 µm or less, 0.50 µm or more and 1.6 µm or less, 0.60 µm or more and 1.6 µm or less, or 0.63 µm or more and 1.6 µm or less.

The minimum value (RaB) of the arithmetic average roughness (Ra) of the surface of the water-insoluble material is, for example, 0.10 µm or more and less than 0.50 µm, although it varies depending on the value of the maximum value (RaA).

The "difference between the maximum value (RaA) and the minimum value (RaB)" is calculated, using the maximum value (RaA) and the minimum value (RaB) calculated by the methods described above, and by subtracting the minimum value (RaB) from the maximum value (RaA). When the difference between the maximum value (RaA) and the minimum value (RaB) is adjusted to 0.30 to 1.50 µm, it is possible to improve the adsorption rate of blood components such as activated leukocytes and inflammatory cytokines. The reason for this is believed to be because the directivity occurs in the irregularities on the material surface. When the difference between the maximum value (RaA) and the minimum value (RaB) is more than 1.50 µm, on the other hand, the irregularities on the material surface become more pronounced, possibly resulting in the risk of the generation of fine particles due to physical factors on the surface. Therefore, it is believed to be not preferred. Accordingly, the difference between the maximum value (RaA) and the minimum value (RaB) is required to be 0.30 to 1.50 µm, and is preferably 0.33 to 1.30 µm, more preferably 0.33 to 1.00 µm, still more preferably 0.35 to 1.00 µm, and yet still more preferably 0.40 to 1.00 µm. Any preferred lower limit value can be combined with any preferred upper limit.

When the water-insoluble material is fibers, the direction of measurement of the laser microscope in which the arithmetic average roughness (Ra) of the surface of the water-insoluble material is minimum, may be, for example, the fiber longitudinal direction. When the value of the arithmetic average roughness (Ra) in the fiber longitudinal direction is lower than that in the fiber transverse direction, it is possible to allow leukocyte components with phagocytic capacity to more efficiently recognize the fibers and to improve the adsorption performance, while reducing the generation of fine particles.

The term "direction of measurement" refers to the direction of each line segment to be extracted on each image, at the time of calculating the above-described arithmetic average roughness by analyzing the image of the captured subject with the line roughness analysis function.

Figure 2:
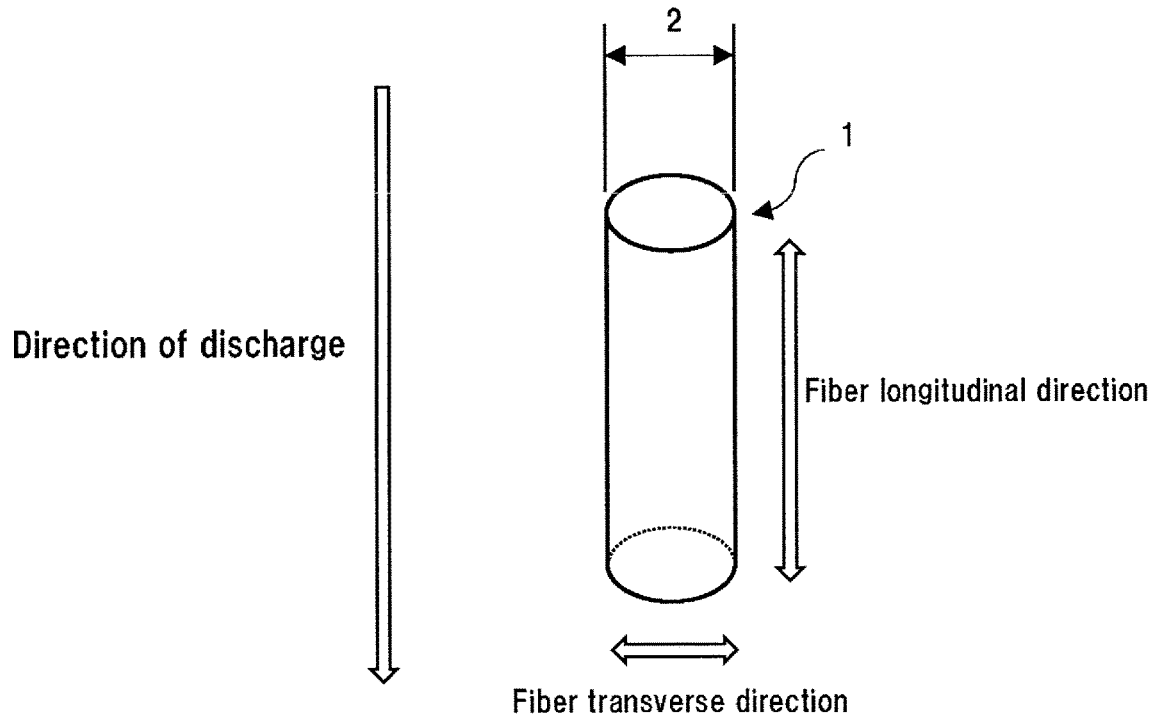
FIG. 2 is a diagram illustrating the fiber longitudinal direction and the fiber transverse direction.

The term "fiber longitudinal direction" refers to the travelling direction (direction of discharge) when the fiber is discharged by spinning, as shown in FIG. 2. Further, the term "fiber transverse direction" refers to the direction orthogonal to the travelling direction when the fiber is discharged, as shown in FIG. 2.

When the water-insoluble material is particles, the direction of measurement of the laser microscope in which the arithmetic average roughness (Ra) of the surface of the water-insoluble material is minimum, may be, for example, the direction orthogonal to the direction of measurement in which the arithmetic average roughness (Ra) has the maximum value (RaA).

The shape of the material surface (arithmetic average roughness) can be adjusted as appropriate, for example, by controlling the production process of the water-insoluble material, or the substrate concentration, reaction time or reaction temperature at the time of introducing a ligand containing an amide group or an amino group, or the like. The ligand or the like to be introduced may be, for example, a chloroacetamidomethyl group, but not particularly limited thereto. At the time of introducing a chloroacetamidomethyl group to the surface of the water-insoluble material, the maximum value (RaA) of the arithmetic average roughness (Ra) tends to increase as the reaction proceeds. As the substrate concentration increases, the value of the maximum value (RaA) of the arithmetic average roughness (Ra) tends to increase, but the value of the minimum value (RaB) of the arithmetic average roughness (Ra) also tends to increase. As a result, the difference between the maximum value (RaA) and the minimum value (RaB) tends to decrease.

In one example, a ligand containing a functional group having an anionic charge or a functional group having a cationic charge may be bound to the surface of the water-insoluble material. In a preferred example, a ligand containing an amino group may be bound to the surface of the water-insoluble material.

The term "ligand" refers to a compound that binds to the surface of the water-insoluble material, and the chemical structure thereof is not particularly limited, as long as the compound contains a functional group having an anionic charge or a functional group having a cationic charge. The ligand may be, for example, a compound containing a sulfonic acid group or a carboxyl group, which is an anionic functional group, or a compound containing an amino group, which is a cationic functional group. In one example, the ligand is preferably a compound containing a cationic functional group, particularly, a compound containing an amino group. The ligand may contain, as the above-described functional group, a combination of a plurality of the same or different functional groups. The ligand may further contain a neutral functional group as long as it contains the anionic functional group or the cationic functional group described above. For example, a compound (such as tetraethylenepentamine to which a para(p)-chlorophenyl group is bound) in which a neutral functional group such as one described below is bound to a compound containing an anionic functional group or a cationic functional group is included in the definition of the ligand, and the neutral functional group may be, for example: an alkyl group such as methyl group or ethyl group; or an aryl group such as phenyl group, a phenyl group substituted with an alkyl group (e.g., para(p)-methylphenyl group, meta(m)-methylphenyl group, ortho(o)-methylphenyl group, para(p)-ethylphenyl group, meta(m)-ethylphenyl group or ortho(o)-ethylphenyl group) or a phenyl group substituted with a halogen atom (e.g., para(p)-fluorophenyl group, meta(m)-fluorophenyl group, ortho(o)-fluorophenyl group, para(p)-chlorophenyl group, meta(m)-chlorophenyl group or ortho(o)-chlorophenyl group). In this example, the neutral functional group may be bound to the ligand directly, or may be bound via a spacer (the spacer involved in this binding is also referred to as "spacer 1"). The spacer 1 may be, for example, a urea bond, an amide bond or a urethane bond.

Examples of the "amino group" include: amino groups derived from primary amines such as methylamine, ethylamine, propylamine, butylamine, pentylamine, hexylamine, heptylamine, octyl amine and dodecyl amine; amino groups derived from secondary amines such as methylhexylamine, diphenyl methylamine and dimethylamine; amino groups derived from amines containing an unsaturated alkyl chain such as allylamine; amino groups derived from tertiary amines such as trimethylamine, triethylamine, dimethylethylamine, phenyldimethylamine and dimethylhexylamine; amino groups derived from amines containing an aromatic ring such as 1-(3-aminopropyl)imidazole, pyridine-2-amine and 3-sulfoaniline; and amino groups derived from compounds (hereinafter "polyamines") in which two or more amino groups are bound via one or more alkyl chains, aromatic compounds, heterocyclic compounds, homocyclic compounds and the like such as tris(2-aminoethyl)amine, ethylenediamine, diethylenetriamine, triethylenetetramine, tetraethylenepentamine, pentaethylenehexamine, hexaethyleneheptamine, heptaethyleneoctamine, octaethylenenonamine, dipropylenetriamine, polyethyleneimine, N-methyl-2,2'-diaminodiethylamine, N-acetylethylenediamine and 1,2-bis(2-aminoethoxyethane). The amino groups in the polyamine structure are more preferably amino groups derived from primary amines or secondary amines. The polyamine may be a linear, branched, or cyclic polyamine. Further, the polyamine may contain a structure as shown below as a substituent on a basic nitrogen atom. Examples of the structure include: alkyl groups having 1 to 10 carbon atoms; unsaturated alkyl chains such as vinyl group and allyl group; phenyl group; aromatic substituents such as naphthyl group and anthracyl group; and heterocyclic substituents such as imidazolyl group, pyridyl group and piperidyl group.

In one example, the water-insoluble material and a ligand containing an amino group such as an amino group derived from a polyamine may be bound to each other directly, or may be bound via a spacer derived from a reactive functional group, interposed between the water-insoluble material and the ligand (the spacer involved in this binding is "spacer 2"). The spacer 2 may be any spacer as long as it is one having an electrically neutral chemical bond such as a urea bond, an amide bond, an ether bond, an ester bond, a urethane bond or the like, and is preferably a spacer having an amide bond or a urea bond.

Examples of the reactive functional group that mediates the binding between the water-insoluble material and the ligand include: active halogen groups, including haloalkyl groups such as halomethyl groups and haloethyl groups, haloacyl groups such as haloacetyl groups and halopropionyl groups and haloacetamidoalkyl groups such as haloacetamidomethyl groups and haloacetamidoethyl groups; epoxide group; carboxyl group; isocyanic acid group; thioisocyanic acid group; and acid anhydride groups. The reactive functional group is preferably an active halogen group, and more preferably a haloacetamidoalkyl group, particularly, a haloacetamidomethyl group, because of its moderate reactivity. Specific examples of the water-insoluble material to which such a reactive functional group is introduced include a polystyrene to the surface of which chloroacetamidomethyl groups are introduced, and a polysulfone to the surface of which chloroacetamidomethyl groups are introduced.

The reactive functional group can be bound to the water-insoluble material, by allowing the water-insoluble material to react with a suitable reagent, in advance. For example, when the sea component of the sea-island composite fibers constituting the water-insoluble material is polystyrene, and the reactive functional group is chloroacetamidomethyl group, the polystyrene can be reacted with N-hydroxymethyl-2-chloroacetamide, to obtain a polystyrene to which chloroacetamidomethyl groups are bound. The polystyrene to which chloroacetamidomethyl groups are bound can be reacted, for example, with tetraethylenepentamine containing amino groups, to obtain a polystyrene to which tetraethylenepentamine is bound via acetamidomethyl groups. In this example, the acetamidomethyl group corresponds to the spacer 2, and the tetraethylenepentamine corresponds to the ligand. The materials of the sea component and the island component of the water-insoluble material, the spacers (spacer 1 and spacer 2), and the ligand can be combined arbitrarily. Examples of the constituent components of the water-insoluble material to which a ligand is bound include: a polystyrene to which a ligand containing a polyamine such as ethylenediamine, diethylenetriamine, triethylenetetramine or tetraethylenepentamine is bound via an acetamidomethyl group; and a polysulfone to which a ligand containing a polyamine such as ethylenediamine, diethylenetriamine, triethylenetetramine or tetraethylenepentamine is bound via an acetamidomethyl group.

In the water-insoluble material, the amino group content is not particularly limited. However, the amino group content is preferably 0.20 mmol or more per 1 g in dry weight of the water-insoluble material from the viewpoint of improving the adsorption performance for organic substances having an electric charge such as blood components. In view of the impact on the pH of blood, the amino group content is preferably 3.00 mmol or less per 1 g in dry weight of the water-insoluble material. That is, the amino group content is preferably 0.20 to 3.00 mmol, more preferably 0.50 to 2.00 mmol, and still more preferably 0.70 to 1.50 mmol, per 1 g in dry weight of the water-insoluble material. Any preferred lower limit value can be combined with any preferred upper limit.

The amino group content can be measured by the acid-base titration method using hydrochloric acid or an aqueous solution of sodium hydroxide.

The blood treatment material can be produced, for example, by the following method, but not limited thereto.

To a solution obtained by dissolving an amide compound such as N-methylol-α-chloroacetamide containing an alkyl halide group and a methylol group, an aldehyde compound such as paraformaldehyde as a cross-linking agent and a catalyst for a cross-linking reaction, sea-island composite fibers are added, followed by stirring, to prepare amidomethyl group-bonded sea-island composite fibers. The fibers are then retrieved, and subsequently, the amidomethyl group-bonded sea-island composite fibers prepared above and a catalyst such as triethylamine are added to a dimethyl sulfoxide (hereinafter DMSO) solution in which a compound such as tetraethylenepentamine containing an amino group is dissolved, to allow a reaction to occur. After retrieving the fibers, the fibers are washed with water, to obtain sea-island composite fibers to the surface of which a ligand containing an amino group is bound. In this example, the ligand containing an amino group corresponds to the compound such as tetraethylenepentamine containing an amino group.

Examples of the solvent to be used in the production of the amidomethyl group-bonded sea-island composite fibers when the sea component is polystyrene, include nitrobenzene, nitropropane, chlorobenzene, toluene and xylene. The solvent is preferably nitrobenzene or nitropropane.

Examples of the cross-linking agent to be used in the production of the amidomethyl group-bonded sea-island composite fibers include aldehyde compounds such as paraformaldehyde, acetaldehyde and benzaldehyde.

Examples of the catalyst for a cross-linking reaction to be used in the production of the amidomethyl group-bonded sea-island composite fibers include: sulfuric acid; hydrochloric acid; nitric acid; and Lewis acids such as aluminum (III) halides, for example, aluminum (III) chloride and iron (III) halides, for example, iron (III) chloride. Sulfuric acid or iron (III) chloride is preferably mixed.

The concentration of the catalyst in the mixed liquid to be used in the production of the amidomethyl group-bonded sea-island composite fibers is preferably 5 to 80 wt %, and more preferably 30 to 70 wt %.

The impregnation temperature in the production of the amidomethyl group-bonded sea-island composite fibers is preferably 0 to 90° C., and more preferably 5 to 40° C.

The impregnation time in the production of the amidomethyl group-bonded sea-island composite fibers is preferably 1 minute to 120 hours, and more preferably 5 minutes to 24 hours.

Examples of the solvent to be used in the production of the sea-island composite fibers to the surface of which a ligand containing an amino group is bound, include N,N-dimethylformamide, diethyl ether, dioxane, tetrahydrofuran and dimethyl sulfoxide. The solvent is preferably dimethyl sulfoxide.

Examples of the catalyst to be used in the production of the sea-island composite fibers to the surface of which a ligand containing an amino group is bound, include: organic bases such as triethylamine and 1,4-diazabicyclo[2.2.2]octane; and inorganic bases such as sodium hydroxide. The catalyst is preferably an organic base such as triethylamine.

The concentration of the catalyst in the mixed liquid to be used in the production of the sea-island composite fibers to the surface of which a ligand containing an amino group is bound, is preferably 50 to 1,000 mM, and more preferably 300 to 700 mM.

The impregnation temperature in the production of the sea-island composite fibers to the surface of which a ligand containing an amino group is bound, is preferably 15 to 80° C., and more preferably 40 to 60° C.

The impregnation time in the production of the sea-island composite fibers to the surface of which a ligand containing an amino group is bound, is preferably 30 minutes to 24 hours, and more preferably 1 hour to 8 hours.

The blood treatment material may be preferably used as a carrier to be packed into a blood purification column. When performing extracorporeal circulation for the purpose of treating inflammatory diseases, in particular, the blood treatment material is suitably used as a carrier for the adsorption and removal of activated leukocytes and/or inflammatory cytokines. When using the blood purification column containing the blood treatment material as a column for extracorporeal circulation in a blood purification therapy, blood drawn from the body may be directly passed through the column, or the column may be used in combination with a plasma separation membrane or the like.

The term "inflammatory diseases" refers to the entire group of diseases in which an inflammatory reaction is induced in the body. Examples of inflammatory diseases include systemic lupus erythematosus, malignant rheumatoid arthritis, multiple sclerosis, ulcerative colitis, Crohn's disease, drug-induced hepatitis, alcoholic hepatitis, type A hepatitis, type B hepatitis, type C hepatitis, type D hepatitis, type E hepatitis, sepsis such as sepsis induced by gram-negative bacteria, sepsis induced by gram-positive bacteria, culture-negative sepsis and fungal sepsis, influenza, acute respiratory distress syndrome (ARDS), acute lung injury (ALI), pancreatitis, idiopathic pulmonary fibrosis (IPF), inflammatory enteritis such as ulcerative colitis and Crohn's disease, blood product transfusion, organ transplant, reperfusion injury after organ transplant, cholecystitis, cholangitis and neonatal blood group incompatibility. Among the inflammatory diseases, those in which a causative agent is released in blood, and thus the therapeutic effect by blood purification can be particularly expected include: drug-induced hepatitis, alcoholic hepatitis, type A hepatitis, type B hepatitis, type C hepatitis, type D hepatitis, type E hepatitis, sepsis such as sepsis induced by gram-negative bacteria, sepsis induced by gram-positive bacteria, culture-negative sepsis and fungal sepsis, influenza, acute respiratory distress syndrome, acute lung injury, pancreatitis and idiopathic pulmonary fibrosis. The applications of the blood purification column are preferably, for example, therapeutic applications for the above-described inflammatory diseases. In particular, more preferred are therapeutic applications for those that are considered as inflammatory diseases which are difficult to treat with drugs alone and in which both activated leukocytes and inflammatory cytokines are involved. Examples of such diseases include sepsis such as sepsis induced by gram-negative bacteria, sepsis induced by gram-positive bacteria, culture-negative sepsis and fungal sepsis, influenza, acute respiratory distress syndrome, acute lung injury and idiopathic interstitial pneumonia.

The blood purification performance of the blood treatment material can be evaluated, for example, by a method in which the interleukin 8 (hereinafter IL-8) adsorption rate is measured. IL-8 is one type of inflammatory cytokine contained in blood components. Since it is known that a markedly high value of IL-8 is observed in blood components in patients with inflammatory diseases, particularly, in patients with diseases developed due to bronchiolitis and virus infection, IL-8 is suitable as a blood component for evaluating the blood purification performance. A higher IL-8 adsorption rate can be judged as having a higher blood purification performance of the blood treatment material.

Further, the blood purification performance of the blood treatment material can be evaluated, for example, by another method in which the removal rate of activated leukocytes is measured. Examples of the method of calculating the removal rate of activated leukocytes include a method in which a container having an inlet and an outlet is packed with a material for purifying blood, a liquid containing activated leukocytes is allowed to pass through the container, and the removal rate of activated leukocytes is calculated from the changes in the concentrations thereof at the inlet and the outlet.

From the viewpoint that activated leukocytes are cells and the measured results of the removal rate thereof include variations, it can be judged that activated leukocytes are significantly removed if the activated leukocyte removal rate is 6% or more. When the water-insoluble material is fibers, however, the activated leukocyte removal rate is preferably 80% or less, because, when activated leukocytes are excessively adsorbed in the gaps between the fibers, there is a risk of causing clogging, possibly resulting in an increase in circulation pressure.

If the strength of the blood treatment material is insufficient during the adsorption treatment using the blood treatment material, there is a risk that the friction with liquid causes the fiber surface to peel off as fine particles due to brittle fracture, and the fine particles to mix into the solution that has passed through the material. When using the blood treatment material for extracorporeal circulation, in particular, there is a risk that the thus generated fine particles may enter the body, and thus, the installation of a filter is required separately, for ensuring safety, making the management complicated. Therefore, it is desirable to prevent the brittle fracture of the blood treatment material from occurring as much as possible, during the extracorporeal circulation. Whether the brittle fracture is occurring or not can be evaluated by measuring the number of fine particles generated from the blood treatment material.

The number of fine particles generated from the blood treatment material can be measured with reference to General Test Methods, 6. 07, Insoluble Particulate Matter Test for Injections (Method 1: Light obscuration particle count test; pp. 1-2), listed in Japanese Pharmacopoeia, Fifteenth revision, (Notification of the Ministry of Health, Labor and Welfare, No. 285, Mar. 31, 2006). Specifically, the number of fine particles generated can be measured, for example, by a method in which a certain area of the blood treatment material is cut out and packed into a cell, water in the cell is stirred to extract fine particles, and the number of fine particles obtained by the extraction is measured.

The blood purification column is characterized by including the blood treatment material described above.

The term "blood purification column" refers to a column which has at least a liquid inlet portion, a casing portion and a liquid outlet portion, and in which the casing portion is packed with the blood treatment material. The column may be, for example, a radial flow type column.

The blood purification column can be used for the application of purifying or removing a blood component of interest from a liquid containing blood components and the like since the blood purification column is capable of adsorbing a blood component(s) and the like from the liquid, by allowing the liquid to pass therethrough. For example, the blood purification column can be used for the separation of a specific blood component and the like. The blood purification column is suitably used, particularly, for the application of adsorbing and removing humoral factors in blood and/or cells in blood, among blood components. Above all, the column is particularly suitably used as a blood purification column for the adsorption and removal of inflammatory cytokines and/or activated leukocytes.

The container of the blood purification column may be in any shape, as long as the container has an inlet portion and an outlet portion for a liquid (hereinafter "liquid") containing blood components and the like, and a casing portion, and has a shape which allows the casing portion to be packed with the blood treatment material. In one example, the container of the blood purification column may be, for example, a container whose interior can be packed with the blood treatment material (hereinafter "cylinder") that has been wound around a pipe and formed into a cylindrical form, wherein the liquid enters from the outer periphery of the cylinder and flows toward the inner side of the cylinder, and thereafter exits out of the container, or wherein the liquid enters from the inner side of the cylinder and flows toward the outer side of the cylinder, and thereafter exits out of the container. From the viewpoints of improving the production efficiency and reducing the short pass of the treatment liquid, the container preferably has a structure in which the blood treatment material is wound around a pipe having holes on the side surface thereof. Specifically, the container may be, for example, a radial flow type container including: a central pipe with holes which are provided on the side surface in the longitudinal direction of the pipe, for allowing the supplied liquid to flow therethrough; the blood treatment material which is packed around the central pipe, and which adsorbs a target substance contained in the liquid; a plate which is arranged to communicate with the upstream end of the central pipe so that the flown-in liquid passes through the interior of the central pipe, and to prevent the liquid from coming into contact with the blood treatment material without passing through the central pipe; and a plate which is arranged to block the downstream end of the central pipe, and to fix the water-insoluble material to the space around the central pipe. Further, the container may be, for example, in the form of a cylinder, or in the form of a rectangular prism such as a triangular prism, a quadrangular prism, a hexagonal prism or an octagonal prism, but the shape of the container is not limited to such a structure. In another example, the container of the blood purification column can be a container having a cylindrical space in the interior thereof, which space can be packed with the blood treatment material that has been cut into a circular shape, wherein the container has a liquid introduction port and a liquid discharge port. Specifically, the container may be, for example, a container which includes, in the interior thereof: a plate having a liquid introduction port provided for introducing the supplied liquid; a plate having a liquid discharge port provided for discharging the supplied liquid; and a cylindrical casing portion packed with the blood treatment material that has been cut into a circular shape; wherein the container has the liquid introduction port and the liquid discharge port. In this example, the shape of the blood treatment material is not limited to a circular shape, and can be changed as appropriate to an arbitrary shape, for example, in the form of an ellipsoid, a polygon such as a triangle or a quadrangle, or a trapezoid, depending on the shape of the container of the blood purification column.

The container of the blood purification column may be, for example, a container made of glass, a plastic or resin, stainless steel or the like, and the size of the container is selected as appropriate depending on the purpose of use. There is no particular limitation on the size and the like of the container of the blood purification column. However, in view of the operability and in disposal at clinical sites and measuring locations, the container is preferably made of a plastic or resin, preferably has a size capable of being easily held in a hand, and preferably has a height of the entire blood purification column of 1 cm or more and 30 cm or less, an outer diameter of 1 cm or more and 10 cm or less, and an internal volume of 200 $cm^3$ or less. In Examples to be described later, a blood purification column having an internal volume of 0.94 $cm^3$ (inner diameter: 1.0 cm×height: 1.2 cm) and an outer diameter of 2.0 cm is used because of the ease of measurement, but the column is not limited thereto.

The blood treatment material is preferably laminated and packed into the blood purification column. The term "to laminate" refers to layering two or more layers of the blood treatment material, in close contact. The blood treatment material can be laminated and packed into the column, for example, by a method in which a plurality of layers of the blood treatment material processed in the form of sheets are layered one on another, as when forming an axial flow column; and a method in which the blood material processed in the form of a sheet is wound around a pipe with holes, as when forming a radial flow column.

The content to be packed into the blood purification column may be the blood treatment material alone, or may be a combination with any of other water-insoluble materials and various spacers. Examples of the spacer include fibers formed in the form of sheets such as knitted fabrics, woven fabrics and nonwoven fabrics; membranes; beads; and hydrogels.

EXAMPLES

Our blood treatment material will now be described in specific detail by way of Examples. However, this disclosure is in no way limited to these Examples.

Preparation of Fiber A

Polystyrene (weight average molecular weight: 180,000; manufactured by PS Japan Corporation) having a melt flow rate (unit: g/10 min; hereinafter "MFR") of 18 g/10 min, as the sea component, and polypropylene (manufactured by Prime Polymer Co., Ltd.) having an MFR of 12 g/10 min, as the island component were used. Both components were separately melted and metered, and allowed to flow into a spin pack incorporating a sea-island composite spinneret in which 700 island-component distribution holes had been drilled per one discharge hole, to form a sea-island composite flow, and melt extruded. The island ratio was controlled to 50 wt %, to obtain sea-island composite fibers A (hereinafter "fiber A") having a single fiber fineness of 3.0 dtex, fiber diameter of 20 µm, number of islands of 700 and number of filaments of 36.

Preparation of Fiber B

Polystyrene (weight average molecular weight: 260,000; manufactured by PS Japan Corporation) having an MFR of 2 g/10 min, as the sea component, and polypropylene (manufactured by Prime Polymer Co., Ltd.) having an MFR of 12 g/10 min, as the island component were used. Both components were separately melted and metered, and allowed to flow into a spin pack incorporating a sea-island composite spinneret in which 700 island-component distribution holes had been drilled per one discharge hole, to form a sea-island composite flow, and melt extruded. The island ratio was controlled to 50 wt %, to obtain sea-island composite fibers B (hereinafter "fiber B") having a single fiber fineness of 3.0 dtex, fiber diameter of 20 μm, number of islands of 700 and number of filaments of 36.

Preparation of Fiber C

A mixture of 90% by mass of polystyrene (weight average molecular weight: 180,000; manufactured by PS Japan Corporation) having an MFR of 18 g/10 min and 10% by mass of polypropylene having an MFR of 12 g/10 min (manufactured by Prime Polymer Co., Ltd.), as the sea component, and polypropylene (manufactured by Prime Polymer Co., Ltd.) having an MFR of 12 g/10 min, as the island component were used. Both components were separately melted and metered, and allowed to flow into a spin pack incorporating a sea-island composite spinneret in which 700 island-component distribution holes had been drilled per one discharge hole, to form a sea-island composite flow, and melt extruded. The island ratio was controlled to 50 wt %, to obtain sea-island composite fibers C (hereinafter "fiber C") having a single fiber fineness of 3.0 dtex, fiber diameter of 20 μm, number of islands of 700 and number of filaments of 36.

Preparation of Fiber D

A material composed of a core component and a sheath component, wherein the core component is polypropylene (manufactured by Prime Polymer Co., Ltd.) having an MFR of 12 g/10 min, and the sheath component is polystyrene (weight average molecular weight: 180,000, manufactured by PS Japan Corporation) having an MFR of 18 g/10 min, was used as the island component; and polyethylene terephthalate (copolymerized PET 1, melt viscosity: 45 Pas) obtained by copolymerizing 8.0% by mole of 5-sodium sulfoisophthalic acid and 10 wt % of polyethylene glycol having a number average molecular weight of 1,000, was used as the sea component. Both components were separately melted and metered, and allowed to flow into a spin pack, to form a sea-island composite flow, and melt extruded. The above-described spin pack includes a metering plate having a plurality of metering holes for metering the respective polymer components, and a distribution plate having a plurality of distribution holes drilled in a merging groove in which polymers discharged from the metering holes merge, and incorporates a sea-island composite spinneret designed such that the sheath component in the island component forms slit-like shapes. The core/sheath ratio was controlled to 50/50 (v/v), and the sea/island ratio was controlled to 30/70 (v/v), to obtain sea-island composite fibers having a single fiber fineness of 5.0 dtex, fiber diameter of 30 μm, and number of filaments of 24. Subsequently, 1 g of the resulting sea-island composite fibers were immersed in 50 cm³ of chloroform at room temperature, left to stand overnight to dissolve the sea component of the sea-island composite fibers, and then washed with methanol and ion exchanged water, in this order, to obtain core-sheath composite slit fibers D (hereinafter "fiber D") having number of slits of 16 and a slit gap of 2 μm, as the core-sheath component of the sea-island composite fibers.

Preparation of Knitted Fabric A

Using the fiber A, the density adjustment scale of a circular knitting machine (model name: circular knitting machine MR-1; manufactured by Maruzen Sangyo Co., Ltd.) was adjusted to prepare a circular knitted fabric A (hereinafter "knitted fabric A") having a basis weight of 56 g/m² and a bulk density of 0.20 g/cm³.

Preparation of Knitted Fabric B

Using the fiber B, the density adjustment scale of a circular knitting machine (model name: circular knitting machine MR-1; manufactured by Maruzen Sangyo Co., Ltd.) was adjusted to prepare a circular knitted fabric B (hereinafter "knitted fabric B") having a basis weight of 55 g/m² and a bulk density of 0.20 g/cm³.

Preparation of Knitted Fabric C

Using the fiber C, the density adjustment scale of a circular knitting machine (model name: circular knitting machine MR-1; manufactured by Maruzen Sangyo Co., Ltd.) was adjusted to prepare a circular knitted fabric C (hereinafter "knitted fabric C") having a basis weight of 54 g/m² and a bulk density of 0.19 g/cm³.

Preparation of Knitted Fabric D

Using the fiber D, the density adjustment scale of a circular knitting machine (model name: circular knitting machine MR-1; manufactured by Maruzen Sangyo Co., Ltd.) was adjusted to prepare a circular knitted fabric D (hereinafter "knitted fabric D") having a basis weight of 70 g/m² and a bulk density of 0.22 g/cm³.

Preparation of Blood Treatment Material 1

A quantity of 3.3 g of N-hydroxymethyl-2-chloroacetamide (hereinafter, referred to as "NMCA") was added to a mixed liquid of 26 cm³ of nitrobenzene and 17 cm³ of 98% by weight sulfuric acid, and the mixture was stirred at 10° C. until NMCA was dissolved, to prepare a NMCA solution. Subsequently, 0.2 g of paraformaldehyde (hereinafter "PFA") was added to a mixed liquid of 2 cm³ of nitrobenzene and 1.3 cm³ of 98% by weight sulfuric acid, and the mixture was stirred at 20° C. until PFA was dissolved, to prepare a PFA solution. A quantity of 3.3 cm³ of the PFA solution was cooled to 5° C., and then mixed with 43 cm³ of the NMCA solution. After stirring the resulting mixed liquid for 5 minutes, 1 g of the knitted fabric A was added thereto, and the fabric was impregnated with the mixed liquid for 2 hours. The impregnated knitted fabric A was immersed in 43 cm³ of nitrobenzene at 10° C. to terminate the reaction, and then the nitrobenzene adhered to the knitted fabric A was washed off with methanol.

To a mixed liquid obtained by dissolving 0.2 cm³ of tetraethylenepentamine (hereinafter "TEPA") and 2.9 cm³ of triethylamine in 40 cm³ of DMSO, the knitted fabric A washed with methanol was added as it is, and the fabric was impregnated with the mixed liquid at 40° C. for 3 hours. The knitted fabric A was separated by filtration using a glass filter, and washed with 40 cm³ of DMSO.

To 25 cm³ of DMSO which had been dehydrated and dried with activated molecular sieves 3A, 0.1 g of p-chlorophenyl isocyanate was added in a nitrogen atmosphere, and the resulting mixture was heated to 30° C. Thereafter, the entire amount of the washed knitted fabric A was added to the mixture, and the fabric was impregnated with the mixture for 1 hour. The knitted fabric A was separated by filtration using a glass filter to obtain a blood treatment material 1. Since the blood treatment material 1 is composed of a water-insoluble material, the content of amino groups per 1 g in dry weight of the water-insoluble material contained in the blood treatment material 1, and the arithmetic average roughness (Ra) of the surface of the water-insoluble material contained in the blood treatment material 1, were calculated by analyzing the blood treatment material 1.

Measurement of Content of Amino Groups Contained in Blood Treatment Material 1:

The content of amino groups contained in the blood treatment material 1 was determined by measuring the content of amino groups contained in the blood treatment material 1 by acid-base back titration. To a 200 cm³ eggplant flask, 1.5 g of the blood treatment material 1 was introduced, and the flask was left to stand at 80° C. for 48 hours under normal pressure, in a drying machine, to obtain the dry-treated blood treatment material 1. Subsequently, 1.0 g of the blood treatment material 1 and 50 cm³ of a 6 M aqueous solution of sodium hydroxide were added to a polypropylene container, followed by stirring for 30 minutes, and the blood treatment material 1 was separated by filtration using a filter paper. Thereafter, the blood treatment material 1 was added to 50 cm³ of ion exchanged water, followed by stirring for 30 minutes, and the blood treatment material 1 was separated by filtration using a filter paper. The operation of adding the blood treatment material 1 to ion exchanged water, and performing washing and separation by filtration, was repeated, until the pH of the resulting washing liquid after the filtration of the added ion exchanged water reached 7 to obtain the desalted blood treatment material 1. The desalted blood treatment material 1 was left to stand under vacuum conditions for 8 hours, in a vacuum dryer controlled to 30° C. Subsequently, 1.0 g of the blood treatment material 1 and 30 cm³ of 0.1 M hydrochloric acid were added to a polypropylene container, followed by stirring for 10 minutes. After the stirring, the solution alone was taken out in an amount of 5 cm³, and transferred to a polypropylene container. Thereafter, 0.1 cm³ of a 0.1 M aqueous solution of sodium hydroxide was added dropwise to the taken-out solution. The resulting solution was stirred for 10 minutes, after the dropwise addition, and the pH of the solution was measured. The operation of stirring for 10 minutes after the dropwise addition of the 0.1 M aqueous solution of sodium hydroxide, and measuring the pH, was repeated 100 times in the same manner as described above. The amount of dropwise addition of the 0.1 M aqueous solution of sodium hydroxide required until the pH of the resulting solution exceeded 8.5, was taken as the titer per 1 g. The content of amino groups per 1 g of the blood treatment material 1 was calculated using the titer per 1 g and Equation (2). The result is shown in Table 1.

Amino group content (mmol/g) per 1 g in dry weight of blood treatment material 1={liquid amount (30 cm³) of added 0.1 M hydrochloric acid/liquid amount (5 cm³) of taken-out hydrochloric acid}×titer (cm³/g) per 1 g×concentration (0.1 mol/L) of aqueous solution of sodium hydroxide (2)

Measurement of Arithmetic Average Roughness (Ra) of Surface of Blood Treatment Material 1:

One piece having a size of 2 cm×2 cm was cut out from the blood treatment material 1, and dried in vacuum at 25° C. for 16 hours. An image of the dried blood treatment material 1 was captured at an objective lens magnification of 50 times, using a laser microscope (an ultra-deep 3D-shape measuring microscope, VK-9710, manufactured by Keyence Corporation). Line segments at 10 locations were extracted at random in a sampling length l of 20 μm from the profile of a single fiber in the resulting image such that the respective line segments were not in parallel with each other. The line segments were then analyzed using analysis software installed in VK-9710, in the line roughness mode to measure the arithmetic average roughness (Ra) of the surface at each of the 10 locations (in accordance with JIS B 0601: 2001). The above-described operation was performed for each of the images captured in three different visual fields, Ra was calculated for each of the line segments of the total of 30 locations that had been extracted from the images in the three visual fields, and the maximum value (RaA) and the minimum value (RaB) were obtained from the values of Ra of these 30 locations. In the above measurement, the RaA was obtained from the analysis in the fiber transverse direction, and the RaB was obtained from the analysis in the fiber longitudinal direction. Further, the difference between the thus obtained RaA and RaB was calculated using Equation (3). The results are shown in Table 1. In Table 1, the values of RaA and RaB are values each rounded to the third decimal place, and the value of RaA−RaB is a value rounded to the third decimal place after calculating the difference between RaA and RaB.

Difference between maximum value (RaA) and minimum value (RaB) of surface of blood treatment material 1=maximum value (RaA) of arithmetic average roughness (Ra) of surface of blood treatment material 1−minimum value (RaB) of arithmetic average roughness (Ra) of surface of blood treatment material 1 (3)

Preparation of Blood Treatment Material 2

The same procedure as in the preparation method of the blood treatment material 1 was carried out except that the amount of NMCA added was changed to 3.8 g, to obtain a blood treatment material 2. Since the blood treatment material 2 is composed of a water-insoluble material, the content of amino groups per 1 g in dry weight of the water-insoluble material contained in the blood treatment material 2, and the arithmetic average roughness (Ra) of the surface of the water-insoluble material contained in the blood treatment material 2, were calculated by analyzing the blood treatment material 2.

Measurement of Content of Amino Groups Contained in Blood Treatment Material 2:

The same procedure as for the blood treatment material 1 was carried out, to measure the content of amino groups contained in the blood treatment material 2. The result is shown in Table 1.

Measurement of Arithmetic Average Roughness (Ra) of Surface of Blood Treatment Material 2:

The same procedure as for the blood treatment material 1 was carried out, to measure the values of the arithmetic average roughness (Ra) of the surface of the blood treatment material 2. The maximum value (RaA) of the arithmetic average roughness (Ra) thereof was obtained from the analysis in the fiber transverse direction, and the minimum value (RaB) thereof was obtained from the analysis in the fiber longitudinal direction. The maximum value (RaA), the minimum value (RaB), and the difference between the maximum value (RaA) and the minimum value (RaB) are shown in Table 1.

Preparation of Blood Treatment Material 3

The same procedure as in the preparation method of the blood treatment material 1 was carried out except that the amount of NMCA added was changed to 4.2 g, to obtain a blood treatment material 3. Since the blood treatment material 3 is composed of a water-insoluble material, the content of amino groups per 1 g in dry weight of the water-insoluble material contained in the blood treatment material 3, and the arithmetic average roughness (Ra) of the surface of the water-insoluble material contained in the blood treatment material 3, were calculated by analyzing the blood treatment material 3.

Measurement of Content of Amino Groups Contained in Blood Treatment Material 3:

The same procedure as for the blood treatment material 1 was carried out, to measure the content of amino groups contained in the blood treatment material 3. The result is shown in Table 1.

Measurement of Arithmetic Average Roughness (Ra) of Surface of Blood Treatment Material 3:

The same procedure as for the blood treatment material 1 was carried out, to measure the values of the arithmetic average roughness (Ra) of the surface of the blood treatment material 3. The maximum value (RaA) of the arithmetic average roughness (Ra) thereof was obtained from the analysis in the fiber transverse direction, and the minimum value (RaB) thereof was obtained from the analysis in the fiber longitudinal direction. The maximum value (RaA), the minimum value (RaB), and the difference between the maximum value (RaA) and the minimum value (RaB) are shown in Table 1.

Preparation of Blood Treatment Material 4

The same procedure as in the preparation method of the blood treatment material 1 was carried out except that the knitted fabric B was used instead of the knitted fabric A, and that the amount of NMCA added was changed to 4.7 g to obtain a blood treatment material 4. Since the blood treatment material 4 is composed of a water-insoluble material, the content of amino groups per 1 g in dry weight of the water-insoluble material contained in the blood treatment material 4, and the arithmetic average roughness (Ra) of the surface of the water-insoluble material contained in the blood treatment material 4, were calculated by analyzing the blood treatment material 4.

Measurement of Content of Amino Groups Contained in Blood Treatment Material 4:

The same procedure as for the blood treatment material 1 was carried out, to measure the content of amino groups contained in the blood treatment material 4. The result is shown in Table 1.

Measurement of Arithmetic Average Roughness (Ra) of Surface of Blood Treatment Material 4:

The same procedure as for the blood treatment material 1 was carried out, to measure the values of the arithmetic average roughness (Ra) of the surface of the blood treatment material 4. The maximum value (RaA) of the arithmetic average roughness (Ra) thereof was obtained from the analysis in the fiber transverse direction, and the minimum value (RaB) thereof was obtained from the analysis in the fiber longitudinal direction. The maximum value (RaA), the minimum value (RaB), and the difference between the maximum value (RaA) and the minimum value (RaB) are shown in Table 1.

Preparation of Blood Treatment Material 5

The same procedure as in the preparation method of the blood treatment material 1 was carried out except that the knitted fabric C was used instead of the knitted fabric A to obtain a blood treatment material 5. Since the blood treatment material 5 is composed of a water-insoluble material, the content of amino groups per 1 g in dry weight of the water-insoluble material contained in the blood treatment material 5, and the arithmetic average roughness (Ra) of the surface of the water-insoluble material contained in the blood treatment material 5, were calculated by analyzing the blood treatment material 5.

Measurement of Content of Amino Groups Contained in Blood Treatment Material 5:

The same procedure as for the blood treatment material 1 was carried out, to measure the content of amino groups contained in the blood treatment material 5. The result is shown in Table 1.

Measurement of Arithmetic Average Roughness (Ra) of Surface of Blood Treatment Material 5:

The same procedure as for the blood treatment material 1 was carried out, to measure the values of the arithmetic average roughness (Ra) of the surface of the blood treatment material 5. The maximum value (RaA) of the arithmetic average roughness (Ra) thereof was obtained from the analysis in the fiber transverse direction, and the minimum value (RaB) thereof was obtained from the analysis in the fiber longitudinal direction. The maximum value (RaA), the minimum value (RaB), and the difference between the maximum value (RaA) and the minimum value (RaB) are shown in Table 1.

Preparation of Blood Treatment Material 6

The same procedure as in the preparation method of the blood treatment material 1 was carried out except that the amount of NMCA added was changed to 2.8 g to obtain a blood treatment material 6. Since the blood treatment material 6 is composed of a water-insoluble material, the content of amino groups per 1 g in dry weight of the water-insoluble material contained in the blood treatment material 6, and the arithmetic average roughness (Ra) of the surface of the water-insoluble material contained in the blood treatment material 6, were calculated by analyzing the blood treatment material 6.

Measurement of Content of Amino Groups Contained in Blood Treatment Material 6:

The same procedure as for the blood treatment material 1 was carried out, to measure the content of amino groups contained in the blood treatment material 6. The result is shown in Table 1.

Measurement of Arithmetic Average Roughness (Ra) of Surface of Blood Treatment Material 6:

The same procedure as for the blood treatment material 1 was carried out, to measure the values of the arithmetic average roughness (Ra) of the surface of the blood treatment material 6. The maximum value (RaA) of the arithmetic average roughness (Ra) thereof was obtained from the analysis in the fiber transverse direction, and the minimum value (RaB) thereof was obtained from the analysis in the fiber longitudinal direction. The maximum value (RaA), the minimum value (RaB), and the difference between the maximum value (RaA) and the minimum value (RaB) are shown in Table 1.

Preparation of Blood Treatment Material 7

The same procedure as in the preparation method of the blood treatment material 1 was carried out except that the amount of NMCA added was changed to 4.7 g to obtain a blood treatment material 7. Since the blood treatment material 7 is composed of a water-insoluble material, the content of amino groups per 1 g in dry weight of the water-insoluble material contained in the blood treatment material 7, and the arithmetic average roughness (Ra) of the surface of the water-insoluble material contained in the blood treatment material 7, were calculated by analyzing the blood treatment material 7. The blood treatment material 7 was prepared under the same conditions as in the method of preparing a tetraethylenepentamine-p-chlorophenylated knitted fabric for Example 1 described in WO '764.

Measurement of Content of Amino Groups Contained in Blood Treatment Material 7:

The same procedure as for the blood treatment material 1 was carried out, to measure the content of amino groups contained in the blood treatment material 7. The result is shown in Table 1.

Measurement of Arithmetic Average Roughness (Ra) of Surface of Blood Treatment Material 7:

The same procedure as for the blood treatment material 1 was carried out, to measure the values of the arithmetic average roughness (Ra) of the surface of the blood treatment material 7. The maximum value (RaA) of the arithmetic average roughness (Ra) thereof was obtained from the analysis in the fiber transverse direction, and the minimum value (RaB) thereof was obtained from the analysis in the fiber longitudinal direction. The maximum value (RaA), the minimum value (RaB), and the difference between the maximum value (RaA) and the minimum value (RaB) are shown in Table 1.

Preparation of Blood Treatment Material 8

The same procedure as in the preparation method of the blood treatment material 1 was carried out except that the amount of NMCA added was changed to 5.6 g to obtain a blood treatment material 8. Since the blood treatment material 8 is composed of a water-insoluble material, the content of amino groups per 1 g in dry weight of the water-insoluble material contained in the blood treatment material 8, and the arithmetic average roughness (Ra) of the surface of the water-insoluble material contained in the blood treatment material 8, were calculated by analyzing the blood treatment material 8.

Measurement of Content of Amino Groups Contained in Blood Treatment Material 8:

The same procedure as for the blood treatment material 1 was carried out, to measure the content of amino groups contained in the blood treatment material 8. The result is shown in Table 1.

Measurement of Arithmetic Average Roughness (Ra) of Surface of Blood Treatment Material 8:

The same procedure as for the blood treatment material 1 was carried out, to measure the values of the arithmetic average roughness (Ra) of the surface of the blood treatment material 8. The maximum value (RaA) of the arithmetic average roughness (Ra) thereof was obtained from the analysis in the fiber transverse direction, and the minimum value (RaB) thereof was obtained from the analysis in the fiber longitudinal direction. The maximum value (RaA), the minimum value (RaB), and the difference between the maximum value (RaA) and the minimum value (RaB) are shown in Table 1.

Preparation of Blood Treatment Material 9

The same procedure as in the preparation method of the blood treatment material 1 was carried out except that the knitted fabric D was used instead of the knitted fabric A to obtain a blood treatment material 9. Since the blood treatment material 9 is composed of a water-insoluble material, the content of amino groups per 1 g in dry weight of the water-insoluble material contained in the blood treatment material 9, and the arithmetic average roughness (Ra) of the surface of the water-insoluble material contained in the blood treatment material 9, were calculated by analyzing the blood treatment material 9.

Measurement of Content of Amino Groups Contained in Blood Treatment Material 9:

The same procedure as for the blood treatment material 1 was carried out, to measure the content of amino groups contained in the blood treatment material 9. The result is shown in Table 1.

Measurement of Arithmetic Average Roughness (Ra) of Surface of Blood Treatment Material 9:

The same procedure as for the blood treatment material 1 was carried out, to measure the values of the arithmetic average roughness (Ra) of the surface of the blood treatment material 9. The maximum value (RaA) of the arithmetic average roughness (Ra) thereof was obtained from the analysis in the fiber transverse direction, and the minimum value (RaB) thereof was obtained from the analysis in the fiber longitudinal direction. The maximum value (RaA), the minimum value (RaB), and the difference between the maximum value (RaA) and the minimum value (RaB) are shown in Table 1.

Preparation of Blood Treatment Material 10

SepXiris (registered trademark; manufactured by Baxter Inc., medical device approval number: 22500BZX-00401000) was cut with a pipe cutter, and hollow fibers taken out therefrom were used as a blood treatment material 10. Since the blood treatment material 10 is composed of a water-insoluble material, the content of amino groups per 1 g in dry weight of the water-insoluble material contained in the blood treatment material 10, and the arithmetic average roughness (Ra) of the surface of the water-insoluble material contained in the blood treatment material 10, were calculated by analyzing the blood treatment material 10.

Measurement of Content of Amino Groups Contained in Blood Treatment Material 10:

The same procedure as for the blood treatment material 1 was carried out, to measure the content of amino groups contained in the blood treatment material 10. The result is shown in Table 1.

Measurement of Arithmetic Average Roughness (Ra) of Surface of Blood Treatment Material 10:

One piece of fiber having a length of 5 cm was cut out from the blood treatment material 10, and then the same procedure as for the blood treatment material 1 was carried out, to measure the values of the arithmetic average roughness (Ra) of the surface of the blood treatment material 10. The maximum value (RaA) of the arithmetic average roughness (Ra) thereof was obtained from the analysis in the fiber transverse direction, and the minimum value (RaB) thereof was obtained from the analysis in the fiber longitudinal direction. The maximum value (RaA), the minimum value (RaB), and the difference between the maximum value (RaA) and the minimum value (RaB) are shown in Table 1.

Preparation of Blood Treatment Material 11

Cytosorb (registered trademark; manufactured by CytoSorbents Corporation) was cut with a pipe cutter, and beads taken out therefrom were used as a blood treatment material 11. Since the blood treatment material 11 is composed of a water-insoluble material, the content of amino groups per 1 g in dry weight of the water-insoluble material contained in the blood treatment material 11, and the arithmetic average roughness (Ra) of the surface of the water-insoluble material contained in the blood treatment material 11, were calculated by analyzing the blood treatment material 11.

Measurement of Content of Amino Groups Contained in Blood Treatment Material 11:

The same procedure as for the blood treatment material 1 was carried out, to measure the content of amino groups contained in the blood treatment material 11. The result is shown in Table 1.

Measurement of Arithmetic Average Roughness (Ra) of Surface of Blood Treatment Material 11:

One of the beads of the blood treatment material 11 was taken out, and the same procedure as for the blood treatment material 1 was carried out, to measure the values of the arithmetic average roughness (Ra) of the surface of the blood treatment material 11. The maximum value (RaA), the minimum value (RaB), and the difference between the maximum value (RaA) and the minimum value (RaB), obtained from the analyses of the values of the arithmetic average roughness (Ra), are shown in Table 1.

Preparation of Blood Treatment Material 12

Adacolumn (registered trademark; manufactured by JIMRO Co., Ltd., approval number: 21100BZZ00687000) was cut with a pipe cutter, and beads taken out therefrom were used as a blood treatment material 12. Since the blood treatment material 12 is composed of a water-insoluble material, the content of amino groups per 1 g in dry weight of the water-insoluble material contained in the blood treatment material 12, and the arithmetic average roughness (Ra) of the surface of the water-insoluble material contained in the blood treatment material 12, were calculated by analyzing the blood treatment material 12.

Measurement of Content of Amino Groups Contained in Blood Treatment Material 12:

The same procedure as for the blood treatment material 1 was carried out, to measure the content of amino groups contained in the blood treatment material 12. The result is shown in Table 1.

Measurement of Arithmetic Average Roughness (Ra) of Surface of Blood Treatment Material 12:

One of the beads of the blood treatment material 12 was taken out, and the same procedure as for the blood treatment material 1 was carried out, to measure the values of the arithmetic average roughness (Ra) of the surface of the blood treatment material 12. The maximum value (RaA), the minimum value (RaB), and the difference between the maximum value (RaA) and the minimum value (RaB), obtained from the analyses of the values of the arithmetic average roughness (Ra), are shown in Table 1.

Preparation of Blood Treatment Material 13

The same procedure as in the preparation method of the blood treatment material 1 was carried out except that the amount of NMCA added was changed to 4.7 g, and that the period of time for impregnating the knitted fabric A with the mixed liquid of the NMCA solution and the PFA solution was changed to 90 minutes, to obtain a blood treatment material 13. Since the blood treatment material 13 is composed of a water-insoluble material, the content of amino groups per 1 g in dry weight of the water-insoluble material contained in the blood treatment material 13, and the arithmetic average roughness (Ra) of the surface of the water-insoluble material contained in the blood treatment material 13, were calculated by analyzing the blood treatment material 13.

Measurement of Content of Amino Groups Contained in Blood Treatment Material 13:

The same procedure as for the blood treatment material 1 was carried out, to measure the content of amino groups contained in the blood treatment material 13. The result is shown in Table 1.

Measurement of Arithmetic Average Roughness (Ra) of Surface of Blood Treatment Material 13:

The same procedure as for the blood treatment material 1 was carried out, to measure the values of the arithmetic average roughness (Ra) of the surface of the blood treatment material 13. The maximum value (RaA) of the arithmetic average roughness (Ra) thereof was obtained from the analysis in the fiber transverse direction, and the minimum value (RaB) thereof was obtained from the analysis in the fiber longitudinal direction. The maximum value (RaA), the minimum value (RaB), and the difference between the maximum value (RaA) and the minimum value (RaB) are shown in Table 1.

Preparation of Blood Treatment Material 14

The same procedure as in the preparation method of the blood treatment material 9 was carried out except that the amount of NMCA added was changed to 5.6 g, to obtain a blood treatment material 14. Since the blood treatment material 14 is composed of a water-insoluble material, the content of amino groups per 1 g in dry weight of the water-insoluble material contained in the blood treatment material 14, and the arithmetic average roughness (Ra) of the surface of the water-insoluble material contained in the blood treatment material 14, were calculated by analyzing the blood treatment material 14.

Measurement of Content of Amino Groups Contained in Blood Treatment Material 14:

The same procedure as for the blood treatment material 1 was carried out, to measure the content of amino groups contained in the blood treatment material 14. The result is shown in Table 1.

Measurement of Arithmetic Average Roughness (Ra) of Surface of Blood Treatment Material 14:

The same procedure as for the blood treatment material 1 was carried out, to measure the values of the arithmetic average roughness (Ra) of the surface of the blood treatment material 14. The maximum value (RaA) of the arithmetic average roughness (Ra) thereof was obtained from the analysis in the fiber transverse direction, and the minimum value (RaB) thereof was obtained from the analysis in the fiber longitudinal direction. The maximum value (RaA), the minimum value (RaB), and the difference between the maximum value (RaA) and the minimum value (RaB) are shown in Table 1.

Preparation of Blood Treatment Material 15

A quantity of 4.7 g of NMCA was added to a mixed liquid of 26 cm$^3$ of nitrobenzene and 17 cm$^3$ of 98% by weight sulfuric acid, and the mixture was stirred at 10° C. until NMCA was dissolved, to prepare a NMCA solution. Subsequently, 0.2 g of PFA was added to a mixed liquid of 2 cm$^3$ of nitrobenzene and 1.3 cm$^3$ of 98% by weight sulfuric acid, and the mixture was stirred at 20° C. until PFA was dissolved, to prepare a PFA solution. A quantity of 3.3 cm$^3$ of the PFA solution was cooled to 5° C., and then mixed with 43 cm$^3$ of the NMCA solution. After stirring the resulting mixed liquid for 5 minutes, 1 g of the knitted fabric A was added thereto, and the fabric was impregnated with the mixed liquid for 2 hours. The impregnated knitted fabric A was immersed in 43 cm$^3$ of nitrobenzene at 10° C. to terminate the reaction, and then the nitrobenzene adhered to the knitted fabric A was washed off with methanol.

To a mixed liquid obtained by dissolving 0.2 cm$^3$ of TEPA and 2.9 cm$^3$ of triethylamine in 40 cm$^3$ of DMSO, the knitted fabric A washed with methanol was added as it is, and the fabric was impregnated with the mixed liquid at 40° C. for 3 hours. The knitted fabric A was separated by filtration using a glass filter, and washed with 40 cm$^3$ of DMSO. The knitted fabric A was separated by filtration using a glass filter, to obtain a blood treatment material 15. Since the blood treatment material 15 is composed of a water-insoluble material, the content of amino groups per 1 g in dry weight of the water-insoluble material contained in the blood treatment material 15, and the arithmetic average roughness (Ra) of the surface of the water-insoluble material contained in the blood treatment material 15, were calculated by analyzing the blood treatment material 15. The blood treatment material 15 was prepared under the same conditions as in the method of preparing a tetraethylenepentaminated knitted fabric for Example 2 described in WO '962.

Measurement of Content of Amino Groups Contained in Blood Treatment Material 15:

The same procedure as for the blood treatment material 1 was carried out, to measure the content of amino groups contained in the blood treatment material 15. The result is shown in Table 1.

Measurement of Arithmetic Average Roughness (Ra) of Surface of Blood Treatment Material 15:

The same procedure as for the blood treatment material 1 was carried out, to measure the values of the arithmetic average roughness (Ra) of the surface of the blood treatment material 15. The maximum value (RaA) of the arithmetic average roughness (Ra) thereof was obtained from the analysis in the fiber transverse direction, and the minimum value (RaB) thereof was obtained from the analysis in the fiber longitudinal direction. The maximum value (RaA), the minimum value (RaB), and the difference between the maximum value (RaA) and the minimum value (RaB) are shown in Table 1.

Example 1

Measurement of Numbers of Fine Particles Generated from Blood Treatment Material 1

The blood treatment material 1 was cut into a circular shape having a diameter of 26 mm, introduced into a clean container along with 50 mL of ion exchanged water (filtered water) which had been passed through a HEPA filter with a pore size of 0.3 μm, and mixed 10 times by inversion. Thereafter, the liquid was discharged to wash off fiber waste generated from the edges of the knitted fabric. This washing operation was repeated one more time. The washed blood treatment material 1 was placed on the base plate attached to a stirring-type ultraholder, UHP-25K (manufactured by ADVANTEC Co., Ltd.), an O-ring was placed thereon, then sandwiched between the plate and a cylindrical container (cell) having a diameter of 18 mm, and fixed with base-mounting metal fittings. The liquid outlet of the base plate was sealed with a silicone tube, and 10 mL of filtered water was added thereto with the blood treatment material 1 being on the bottom surface side, and we confirmed that there was no leaking water. A stirring set attached to UHP-25K was installed, and stirring was performed at a rotational speed of 600 rpm for 5 minutes, on a magnetic stirrer, RCN-7 (manufactured by Tokyo Rikakikai Co., Ltd.), in a state where the stirring set was not in contact with the blood treatment material 1. The resulting liquid was collected, and 3 mL of the liquid was measured using a light obscuration automatic particle counter, KL-04 (manufactured by Rion Co., Ltd.). The number of fine particles having a particle size of 5 μm or more per 1 mL, and the number of fine particles having a particle size of 10 μm or more per 1 mL were measured, and taken as the respective numbers of generated fine particles (unit: number of particles/mL). The results are shown in Table 2.

Measurement of Activated Leukocyte Removal Rate of Blood Treatment Material 1:

The blood treatment material 1 was cut into discs having a diameter of 1 cm, and the disc-shaped materials were laminated and packed into a cylindrical column (inner diameter: 1 cm×height: 1.2 cm, outer diameter: 2 cm; made of polypropylene) having an inlet and an outlet for a solution at the upper and lower portions thereof, to prepare a column packed with the blood treatment material 1. Blood from a healthy human volunteer to which LPS had been added to a concentration of 70 EU/mL was activated by shaking at 37° C. and at 65 rpm for 30 minutes. The activated blood was passed through the column prepared above at a flow rate of 0.63 mL/min, and blood samples were collected at the inlet and the outlet of the column. The time point at which the blood entered the column was taken as 0 minute, and the sample at the outlet was collected at the time point 6.5 minutes after the start of passing the blood. The collected samples were analyzed with a multi-item automatic blood cell analyzer, and the activated leukocyte removal rate of the blood treatment material 1 was calculated using Equation (4). The result is shown in Table 2.

Activated leukocyte removal rate (%)=(activated leukocyte concentration ($10^2$ cells/μL) in blood after blood passing test)/(activated leukocyte concentration ($10^2$ cells/μL) in blood before blood passing test) (4)

Measurement of IL-8 Adsorption Rate of Blood Treatment Material 1:

To examine the IL-8 adsorption performance of the blood treatment material 1, the blood treatment material 1 was impregnated with a liquid containing IL-8 for a predetermined period of time and then retrieved, and the IL-8 adsorption rate was measured from the difference between the amounts of IL-8 in the liquid before and after the impregnation. The measurement method is as shown below.

The blood treatment material 1 was cut into discs having a diameter of 6 mm, four of which were placed in a polypropylene container. To the container, fetal bovine serum (hereinafter FBS) prepared to an IL-8 concentration of 2,000 pg/mL was added such that the amount of FBS was 88 mL with respect to 1 $cm^3$ of the blood treatment material 1. The resultant was mixed by inversion in an incubator at 37° C. for one hour, and then the IL-8 concentration in the FBS was measured by an enzyme-linked immunosorbent assay (ELISA). The IL-8 adsorption rate was calculated from the IL-8 concentrations before and after the mixing by inversion, in accordance with Equation (5). The result is shown in Table 2.

IL-8 adsorption rate of blood treatment material 1(%)={IL-8 concentration (pg/mL) before mixing by inversion−IL-8 concentration (pg/mL) after mixing by inversion}/IL-8 concentration (pg/mL) before mixing by inversion×100 (5)

Example 2

The same measurements as in Example 1 were carried out except for using the blood treatment material 2, to measure the numbers of generated fine particles, the activated leukocyte removal rate and the IL-8 adsorption rate. The results are shown in Table 2.

Example 3

The same measurements as in Example 1 were carried out except for using the blood treatment material 3, to measure the numbers of generated fine particles, the activated leukocyte removal rate and the IL-8 adsorption rate. The results are shown in Table 2.

Example 4

The same measurements as in Example 1 were carried out except for using the blood treatment material 4, to measure the numbers of generated fine particles, the activated leukocyte removal rate and the IL-8 adsorption rate. The results are shown in Table 2.

Example 5

The same measurements as in Example 1 were carried out except for using the blood treatment material 5, to measure the numbers of generated fine particles, the activated leukocyte removal rate and the IL-8 adsorption rate. The results are shown in Table 2.

Example 6

The same measurements as in Example 1 were carried out except for using the blood treatment material 13, to measure the numbers of generated fine particles, the activated leukocyte removal rate and the IL-8 adsorption rate. The results are shown in Table 2.

Comparative Example 1

The same measurements as in Example 1 were carried out except for using the blood treatment material 6, to measure the numbers of generated fine particles, the activated leukocyte removal rate and the IL-8 adsorption rate. The results are shown in Table 2.

Comparative Example 2

The same measurements as in Example 1 were carried out except for using the blood treatment material 7, to measure the numbers of generated fine particles, the activated leukocyte removal rate and the IL-8 adsorption rate. The results are shown in Table 2.

Comparative Example 3

The same measurements as in Example 1 were carried out except for using the blood treatment material 8, to measure the numbers of generated fine particles, the activated leukocyte removal rate and the IL-8 adsorption rate. The results are shown in Table 2.

Comparative Example 4

The same measurements as in Example 1 were carried out except for using the blood treatment material 9, to measure the numbers of generated fine particles, the activated leukocyte removal rate and the IL-8 adsorption rate. The results are shown in Table 2.

Comparative Example 5

Measurement of Numbers of Fine Particles Generated from Blood Treatment Material 10:
Thirty-nine pieces of fiber having a length of 10 cm were cut out from the blood treatment material 10, and then the same measurement as in Example 1 was carried out, to measure the numbers of generated fine particles. The results are shown in Table 2.
Measurement of Activated Leukocyte Removal Rate of Blood Treatment Material 10:
One hundred and fifty-seven pieces of fiber having a length of 10 cm were cut from the blood treatment material 10, and then the same measurement as in Example 1 was carried out except that the column to be used was changed to a cylindrical column (inner diameter: 0.5 cm×height: 10 cm, internal volume: 1.9 $cm^3$; made of polycarbonate), to measure the activated leukocyte removal rate. The result is shown in Table 2.
Measurement of IL-8 Adsorption Rate of Blood Treatment Material 10:
The blood treatment material 10 was cut out in a length of 50 cm, and then the same measurement as in Example 1 was carried out, to measure the IL-8 removal rate. The result is shown in Table 2.

Comparative Example 6

Measurement of Numbers of Fine Particles Generated from Blood Treatment Material 11:
A quantity of 0.28 mL of the blood treatment material 11 was taken out, and then the same measurement as in Example 1 was carried out, to measure the numbers of generated fine particles. The results are shown in Table 2.
Measurement of Activated Leukocyte Removal Rate of Blood Treatment Material 11:
A quantity of 1.13 mL of the blood treatment material 11 was taken out, and then the same measurement as in Example 1 was carried out, to measure the activated leukocyte removal rate. The result is shown in Table 2.
Measurement of IL-8 Adsorption Rate of Blood Treatment Material 11:
A quantity of 50 µL of the blood treatment material 11 was taken out, and then the same measurement as in Example 1 was carried out, to measure the IL-8 removal rate. The result is shown in Table 2.

Comparative Example 7

Measurement of Numbers of Fine Particles Generated from Blood Treatment Material 12:
The same measurement as in Example 1 was carried out except that the amount of the blood treatment material 12 used was changed to 0.40 g, to measure the numbers of generated fine particles. The results are shown in Table 2.
Measurement of Activated Leukocyte Removal Rate of Blood Treatment Material 12:
A quantity of 1.63 g of the blood treatment material 12 was taken out, and then the same measurement as in Example 1 was carried out, to measure the activated leukocyte removal rate. The result is shown in Table 2.
Measurement of IL-8 Adsorption Rate of Blood Treatment Material 12:
The same measurement as in Example 1 was carried out except that the amount of the blood treatment material 12 used was changed to 75 mg, to measure the IL-8 removal rate. The result is shown in Table 2.

Comparative Example 8

The same measurements as in Example 1 were carried out except for using the blood treatment material 14, to measure the numbers of generated fine particles, the activated leukocyte removal rate and the IL-8 adsorption rate. The results are shown in Table 2.

Comparative Example 9

The same measurements as in Example 1 were carried out except for using the blood treatment material 15, to measure the numbers of generated fine particles, the activated leukocyte removal rate and the IL-8 adsorption rate. The results are shown in Table 2.

size of 10 μm or more" represents the number per unit volume of fine particles having a particle size of 10 μm or more that have been generated from the blood treatment material; "Activated leukocyte removal rate" represents the removal rate of activated leukocytes that have been adsorbed and removed by the blood treatment material; and "IL-8 adsorption rate" represents the adsorption rate of IL-8, which is one type of inflammatory cytokine, that have been adsorbed and removed by the blood treatment material.

The above results have revealed that our blood treatment material is capable of adsorbing and removing blood com-

TABLE 1

| Examples | Amino Group Content [mmol/g] | Maximum value (RaA) of arithmetic average roughness (Ra) [μm] | Minimum value (RaB) of arithmetic average roughness (Ra) [μm] | Difference (RaA − RaB) between RaA and RaB [μm] |
|---|---|---|---|---|
| Blood Treatment Material 1 | 0.85 | 0.82 | 0.29 | 0.53 |
| Blood Treatment Material 2 | 1.16 | 1.14 | 0.44 | 0.71 |
| Blood Treatment Material 3 | 1.15 | 0.71 | 0.36 | 0.36 |
| Blood Treatment Material 4 | 1.03 | 0.73 | 0.22 | 0.51 |
| Blood Treatment Material 5 | 0.79 | 0.64 | 0.29 | 0.35 |
| Blood Treatment Material 6 | 0.94 | 0.23 | 0.20 | 0.03 |
| Blood Treatment Material 7 | 1.09 | 0.68 | 0.40 | 0.28 |
| Blood Treatment Material 8 | 1.07 | 0.99 | 0.70 | 0.29 |
| Blood Treatment Material 9 | 0.93 | 3.57 | 0.19 | 3.37 |
| Blood Treatment Material 10 | 0.12 | 0.03 | 0.02 | 0.02 |
| Blood Treatment Material 11 | 0.00 | 0.29 | 0.21 | 0.09 |
| Blood Treatment Material 12 | 0.00 | 0.27 | 0.20 | 0.07 |
| Blood Treatment Material 13 | 0.91 | 0.71 | 0.38 | 0.33 |
| Blood Treatment Material 14 | 0.95 | 3.32 | 0.32 | 3.00 |
| Blood Treatment Material 15 | 1.24 | 0.65 | 0.40 | 0.25 |

In Table 1, "Maximum value (RaA) of arithmetic average roughness (Ra)" represents the maximum value (RaA) of the arithmetic average roughness (Ra) of the surface of the water-insoluble material; "Minimum value (RaB) of arithmetic average roughness (Ra)" represents the minimum value (RaB) of the arithmetic average roughness (Ra) of the surface of the water-insoluble material; and "Difference (RaA−RaB) between RaA and RaB" represents the difference between the maximum value (RaA) and the minimum value (RaB) of the arithmetic average roughness (Ra) of the surface of the water-insoluble material.

ponents such as activated leukocytes and IL-8 with a higher efficiency, as compared to a blood treatment material in which the difference between the maximum value (RaA) and the minimum value (RaB) of the arithmetic average roughness (Ra) of the surface of the water-insoluble material is less than 0.30 μm or more than 1.50 μm. Further, it has also been revealed that the number of generated fine particles can be reduced, and thus that the blood treatment material has a high safety.

TABLE 2

| Examples | Number of generated fine particles having particle size of 5 μm or more [particles/mL] | Number of generated fine particles having particle size of 10 μm or more [particles/mL] | Activated leukocyte removal rate [%] | IL-8 adsorption rate [%] |
|---|---|---|---|---|
| Example 1 | 215 | 20 | 39 | 61 |
| Example 2 | 421 | 29 | 44 | 56 |
| Example 3 | 453 | 31 | 42 | 50 |
| Example 4 | 376 | 18 | 43 | 51 |
| Example 5 | 210 | 33 | 44 | 50 |
| Example 6 | 450 | 32 | 38 | 49 |
| Comparative Example 1 | 32 | 3 | 31 | 5 |
| Comparative Example 2 | 344 | 32 | 25 | 41 |
| Comparative Example 3 | 5893 | 659 | 28 | 35 |
| Comparative Example 4 | 6922 | 849 | 28 | 40 |
| Comparative Example 5 | 98 | 3 | 3 | 89 |
| Comparative Example 6 | 156 | 10 | 10 | 90 |
| Comparative Example 7 | 67 | 8 | 35 | 8 |
| Comparative Example 8 | 7302 | 654 | 30 | 26 |
| Comparative Example 9 | 350 | 21 | 29 | 38 |

In Table 2, "Number of generated fine particles having particle size of 5 μm or more" represents the number per unit volume of fine particles having a particle size of 5 μm or more that have been generated from the blood treatment material; "Number of generated fine particles having particle

INDUSTRIAL APPLICABILITY

Since our blood treatment material is capable of adsorbing and removing blood components such as activated leukocytes and inflammatory cytokines, with a high efficiency, the material can be used as an adsorption carrier for use in extracorporeal circulation.

The invention claimed is:

1. A blood treatment material comprising a water-insoluble material in the form of fibers or particles, wherein a difference between a maximum value (RaA) and a minimum value (RaB) of a arithmetic average roughness (Ra) of a surface of said water-insoluble material, as calculated using a laser microscope, is 0.30 to 1.50 μm;
wherein said water-insoluble material is in the form of fibers; and
a direction of measurement of said laser microscope in which said arithmetic average roughness (Ra) of the surface of said water-insoluble material is minimum, is a fiber longitudinal direction.

2. The blood treatment material according to claim 1, wherein said difference is 0.33 to 1.00 μm.

3. The blood treatment material according to claim 1, wherein said maximum value (RaA) is 0.50 μm or more.

4. The blood treatment material according to claim 1,
wherein a ligand containing an amino group is bound to the surface of said water-insoluble material; and
the content of said amino group is 0.20 to 3.00 mmol per 1 g in dry weight of said water-insoluble material.

5. The blood treatment material according to claim 1, wherein said water-insoluble material is in the form of sea-island composite fibers;
a sea component of said sea-island composite fibers is selected from the group consisting of polystyrene, a derivative of polystyrene, polysulfone, a derivative of polysulfone and a mixture thereof; and
an island component of said sea-island composite fibers is selected from the group consisting of polypropylene, polyethylene, a polypropylene/polyethylene copolymer and a mixture thereof.

6. The blood treatment material according to claim 1, wherein the blood treatment material adsorbs and removes activated leukocytes and/or inflammatory cytokines.

7. A blood purification column comprising the blood treatment material according to claim 1.

* * * * *